(12) United States Patent
Grabitz

(10) Patent No.: US 7,399,475 B1
(45) Date of Patent: Jul. 15, 2008

(54) INACTIVATED MICROORGANISMS COMPRISING SUBSTANCES HAVING PHARMACOLOGICAL ACTIVITY

(75) Inventor: Ernst Bernhard Grabitz, Casatenovo (IT)

(73) Assignee: Toner Enterprise Inc., Vaduz (LI)

( * ) Notice: Subject to any disclaimer, the term of this patent is extended or adjusted under 35 U.S.C. 154(b) by 0 days.

(21) Appl. No.: 10/018,451

(22) PCT Filed: Apr. 20, 2000

(86) PCT No.: PCT/EP00/03586

§ 371 (c)(1), (2), (4) Date: Mar. 7, 2002

(87) PCT Pub. No.: WO00/64417

PCT Pub. Date: Nov. 2, 2000

(30) Foreign Application Priority Data

Apr. 22, 1999 (IT) .............................. MI99A0842

(51) Int. Cl.
*A61K 36/064* (2006.01)
*C12N 1/00* (2006.01)

(52) U.S. Cl. ............................ 424/195.15; 424/195.16; 435/41; 435/255.1; 435/942

(58) Field of Classification Search ................. 424/439, 424/442, 451, 455, 457, 780, 195.15, 195.16; 435/41, 255.1, 942
See application file for complete search history.

(56) References Cited

U.S. PATENT DOCUMENTS 5,108,764 A * 4/1992 Craig et al. .................... 426/18
5,288,632 A * 2/1994 Pannell ....................... 435/243
5,968,811 A * 10/1999 Greenshields ............ 435/255.2

FOREIGN PATENT DOCUMENTS

| EP | 0094979 | 11/1983 |
|---|---|---|
| EP | 0899326 | 3/1999 |
| EP | 0904701 | 3/1999 |
| WO | WO9422572 | 10/1994 |

OTHER PUBLICATIONS

Gruenwald, J. et al (eds.) PDR for Herbal Medicines. 1998. Medical Economics company, Montvale, N.J., pp. 836-839.*
Marinoni et al., Horizontal Transfer of Genetic Material among *Saccharomyces* Yeasts, Journal of Bacteriology, Oct. 1999, vol. 181, No. 20, p. 6488-6496.

* cited by examiner

*Primary Examiner*—Ralph Gitomer
*Assistant Examiner*—Kailash C Srivastava
(74) *Attorney, Agent, or Firm*—Abelman, Frayne & Schwab

(57) ABSTRACT

Inactivated microorganisms are described which comprise agents that are pharmacologically active for human or animal organisms. A process for the preparation of said organisms is further described and their use as medicaments, food integrators or nutritional substances in general, for both human and animal alimentation.

21 Claims, No Drawings

INACTIVATED MICROORGANISMS COMPRISING SUBSTANCES HAVING PHARMACOLOGICAL ACTIVITY

SCOPE OF INVENTION

The present invention is related to inactivated microorganisms comprising soluble and/or solubilizable substances having pharmacological activity and/or nutritional substances having pharmacological activity, which are absorbed by the systemic circulation of the human or animal organism. A process for their preparation and their uses thereof are described.

STATE OF THE ART

The compounds generally known as soluble and/or solubilizable substances having pharmacological activity and nutritional substances having pharmacological activity refer to active agents and/or substances which, in order to perform their activity, need to penetrate into the systemic circulation of the animal or human organism.

Soluble and/or solubilizable substances having pharmacological activity comprise, for example, drugs and vaccines.

The nutritional substances having pharmacological activity comprise, for example vitamins, amino acids, and food integrators in general, etc.

Pharmacologically active substances and pharmacologically active nutritional substances that involve oral administration need to reach in an intact and active form at the level of the intestine and, in order to be correctly processed, need to penetrate into the systemic circulation and perform their pharmacological or nutritive function effectively.

The oral administration of drugs presents various serious problems, such as emesis resulting from irritation of the gastro-intestinal mucosa, destruction of certain drugs by digestive enzymes or, on account of the low gastric pH, irregularity in absorption or in peristalsis in the presence of food or of other medicinal preparations. Furthermore, drugs in the gastro-intestinal tract may be metabolized by enzymes of the mucosa, by the intestinal flora or by the liver, before reaching the general circulation.

In particular, the wide pH range that is found in the gastrointestinal tract may affect the rate of absorption, altering the relative concentrations of ionized forms and non-ionized forms.

Consequently, drugs and nutritionally active agents administered by oral route present the serious problem that during their passage through the gastric tract they may lose totally or partially their pharmacological efficacy and/or nutritional activity or their bio-availability in the circulation may be impaired.

A further problem is the thermostability of the active agents. In fact, a procedure of administration of said active agents consists in mixing them with food to facilitate their uptake by humans or by animals. Many food preparations require, at the moment of their administration, heating (in some cases also boiling), and this consequently involves the denaturation or thermo-inactivation of those active agents that are thermolabile.

In addition, drugs and nutrients endowed with marked characteristics of hydrophilicity (solubility in water), such as vitamins C and B12, many antibiotics and antibacterial agents, cannot be administered to fishes on account of their solubility in the aqueous medium, even when mixed to nutrients.

Therefore the technical problem in the current state of the art consists in supplying to the systemic tract of the animal or human organism active compounds, in the form of pharmacologically and/or nutritionally active agents ingested by oral route, which will maintain their own pharmaceutical or nutritive capabilities in an unaltered form, so avoiding the problems due to their passage through the gastric tract. A further problem is the prevention of the alteration of these active agents during preparation.

The patent application EP 0 899326 describes the use of a yeast for the transport and release of exogenous digestive enzymes in the stomach. The addition of exogenous enzymes in the stomach is important, for preventive purposes, in the case of animals undergoing intensive feeding or pharmacological treatments, in that they digest food and drugs, inactivating the latter. The microorganisms thus obtained, are mixed in the food compositions and start pre-digestion in the gastric tract.

However the method described in EP 0 899326 refers exclusively to a way to protect digestive enzymes (i.e., substances that are not pharmacologically or nutritionally active) and to release them in the stomach and to their use as adjuvants during intensive feeding or intensive pharmacological treatments.

The present invention intends to solve the problem of delivery of active agents (pharmacologically and nutritionally active agents) in a protected form up to the intestine, i.e., to the site of penetration into the systemic circulation and preventing, up to that moment, any active system to be modified, inactivated or even partially digested by digestive enzymes and by the gastric environment.

SUMMARY OF THE INVENTION

The present inventors have solved these technical problems and have obtained inactivated microorganisms comprising soluble and/or solubilizable substances with pharmacological activity (pharmacologically active agents) and/or nutritional substances having pharmacological activity (nutritionally active agents). Said microorganisms are thus modified and used to protect said active agents during their passage through the stomach into the intestine where said active agents are released and absorbed by the systemic circulation of animals or humans.

Hence, according to a first embodiment, the present invention refers to inactivated microorganisms comprising soluble and/or solubilizable substances and/or nutritional substances with pharmacological activity, such as medicinal preparations or vaccines or nutritionally active agents in general such as vitamins, amino acids, etc.

According to a further embodiment, the invention refers to a process for the preparation of inactivated microorganisms according to the invention comprising the steps of:

i) drawing out the endocellular mass of a suitable microorganism by means of hypertonic treatment;

ii) optional chemical or physical inactivation of the microorganism obtained in Step i), which leaves the external membrane of the microorganism unaltered;

iii) intracellular loading of one or more soluble and/or solubilizable substances having pharmacological activity and/or nutritional substances with pharmacological activity into the inactivated microorganism obtained in Step i) or Step ii) by means of hypo- or isotonic treatment.

In the present description isotonic solution means a solution having the same osmotic pressure as the fluid phase of a cell or a tissue and corresponding to the osmotic pressure of a 0.9% NaCl solution (physiologic saline)). Hypertonic and hypotonic solutions have meanings related to this definition (i.e. > or < than a 0.9% NaCl solution, respectively).

According to a further embodiment, in Step i) the microorganic endocellular mass is drawn out by treatment with a hypertonic solution, where the hypertonicity is provided by the pharmacologically active principle itself.

According to yet a further embodiment, the invention refers to a process in which the introduction of the active principle into the microorganism is carried out in the presence of an isotonic solution in Step iii) of the process.

According to a further embodiment, the invention refers to the use of such inactivated and loaded microorganisms in human or animal alimentation, or also as components of feeds or premixes.

The present invention, in addition, refers to a composition comprising an effective quantity of one or more types of organisms prepared according to the invention.

DETAILED DESCRIPTION OF THE INVENTION

The present invention enables administration, by oral route, of soluble and/or solubilizable substances having pharmacological activity and/or nutritional substances having pharmacological activity, incorporated within the cell walls of inactivated, i.e. "killed" microorganisms, capable of protecting their characteristics of structure and activity. The active agents are thus protected on arrival at the level of the intestine and, once released, enter the systemic circulation where they perform their activity.

Microorganisms

The microorganisms used in the process according to the present invention must be microorganisms with a good resistance to chemical and chemico-physical stress. The said microorganisms may be selected also on the basis of the characteristics of affinity and tolerability in regard to the host organisms.

Among known and commercially available microorganisms, the yeast Saccharomyces cerevisiae, for example, is preferred because of its structural resistance to chemical and chemico-physical agents, being able to reach the intestine unaltered, and to release there the active agents where they are taken into the systemic circulation of the animal or human organism.

Some of the microorganisms that can be used are, for example, those which normally are present in the intestinal microflora, such as *Bacillus subtilis* and *Lactobacillus sp.*, which are also readily available on the market.

It is also possible to use the so-called "vulgar" microorganisms, isolated from human faecal material, belonging to the so-called "good" intestinal flora, or from ruminal, enteric or faecal material of the "good" intestinal flora and of other sources of the various animal breeding species. Isolation is carried out using methodologies known in the state of the art, by growing the microflora in nutrient culture and subsequently selecting the colonies on the basis of their morphological and taxonomic characteristics. The characterization of the isolated strains takes place according to commonly used methodologies, for example from the analysis of the Gram colouring, metabolic behaviour, production of characteristic chemical products and the nutritive characteristics.

Other microorganisms that may be advantageously used in the process of the invention, together with some of their sources, appear in "Biochemical Engineering and Biotechnology Handbook", B. Atkinson and F. Mavituna Eds., 1991, MacMillan Publ., Chaps. 6.1, 6.7 and 9.5.

Active Agents

The soluble and/or solubilizable substances having pharmacological activity and the nutritional substances having pharmacological activity according to the invention are defined as follows.

The soluble and/or solubilizable substances having pharmacological activity according to the invention comprise, for example, all pharmaceutical substances, antibiotic, antibacterial, hormones, anti-inflammatory, antiviral, antifungal, antiparassitic agents and other substances, and vaccines provided that they are soluble and/or solubilizable in an aqueous medium.

The nutritional substances having pharmacological activity comprise, for example, vitamins such as ascorbic acid, folic acid, cyanocobalamin, thiamine or $\alpha$-tocopherol, amino acids, or oligoelements such as cofactors and minerals such as zinc or cobalt, food integrators of various kinds, active principles of vegetable origin and/or the substances known as <<nutriceuticals>>, for example, bioflavonoids such as sodium quercetin, catechin, isocatechin, flavans, cyanins, polyphenols, aliphatic polyalcohols, resveratrol, hyperic acid, rutinoids, etc.

Process of Preparation

The preparation of inactivated microorganisms comprising soluble and/or solubilizable substances and/or nutritional substances having pharmacological activity according to the invention comprises the steps of:

i) drawing out the endocellular mass of an appropriate microorganism by means of hypertonic treatment;

ii) optional chemical or physical inactivation of the microorganism obtained in Step i), which leaves the external membrane of the microorganism unaltered;

iii) intracellular loading of one or more soluble and/or solubilizable substances having pharmacological activity and/or nutritional substances having pharmacological activity in the inactivated microorganism obtained in Step i) or Step ii) by means of hypo- or isotonic treatment.

Before the drawing out step (Step i), microorganisms can be grown in appropriate fermenters, according to the methods and conditions known in the state of the art, separating the microrganic mass from the culture medium at the end of the growth phase, by means of filtration or centrifugation. An example of the operating conditions is provided in "Biochemical Engineering and Biotechnology Handbook", B. Atkinson and F. Mavituna Eds., 1991, MacMillan Publ., Chap. 6.7.

In Step i) the endocellular mass is squeezed out of the microrganic cell walls by means of a hypertonic treatment.

Step i) is performed by resuspension of the microrganic mass in a hypertonic aqueous solution. Hypertonicity can also be achieved by gradually increasing the salt concentration at the hypertonic endpoint.

The hypertonic aqueous solution may comprise:

NaCl in concentrations higher than 0.2 M, preferably 1.0 M;

optionally the citrate ion, which contributes to the enlargement of the membrane pores; although not strictly indispensable, it is preferred that sodium citrate is present in concentrations ranging from 0.03 and 0.1 M, preferably 0.05 M.

Preferably, the aforesaid hypertonic solution comprises NaCl 1.0 M and sodium citrate 0.05 M.

An appropriate antibacterial and/or fixative agent may be possibly added, such as polyphosphates or para-benzoates, formaldehyde or pentaraldehyde.

The suspension obtained is stirred at a temperature ranging from 2 to 40° C., preferably at 25° C., for a period ranging from 2 hours to 4 days, preferably 16 hours, to complete emptying of the microorganisms in such a way that the endocellular content is extruded into the hypertonic medium.

The so treated microorganisms are reduced to the cell walls alone and are smaller than the alive microorganisms; they presents enlarged membrane pores. Empty cell walls may be separated from the endocellular mass by means of techniques known in the state of the art, such as filtration or centrifugation.

The control to ensure that the endocellular mass has been removed to leave just the cell walls may be conveniently performed by morphological microscopic evaluation of the cell walls, which must appear smaller and shrivelled.

The suspension medium (i.e. the hypertonic buffer and the squeezed out endocellular content) can be separated from the microorganisms cell walls, by centrifugation at 2.000-12.000 r.p.m., preferably 4.500 r.p.m (corresponding to about 4600 R.C.F.).

The centrifugates may be optionally washed. In particular, aliquots are used in analytical control to evaluate the quantity of incorporated active agent.

In Step ii), emptied microorganisms may be furtherly inactivated, i.e. killed, by means of appropriate chemical or physical treatment. This treatment may not be required for certain microorganisms, because the hypertonic treatment of Step i) may be sufficient for inactivation. Consequently, Step ii) is carried out only after checking the viability of microorganisms after Step i).

Among the chemical methods preferably used for microorganisms having cells walls that are easily heat-degradable, it is possible to use treatment with disinfectant or fixing substances, such as formalin (formaldehyde) or glutaraldehyde, at concentrations of 0.05-0.2 mg/l, for a time ranging from 5 minutes to 12 hours, preferably at the concentration of 0.1 mg/l, for 6-8 hours.

The chemical inactivation can take place also during the Step i), by adding the above-mentioned disinfectant and/or fixing substances to the hypertonic solution. Physical treatment preferably comprises exposure to UV radiation and thermal inactivation by heating the suspension obtained from Step i) to a temperature of between 55 and 65° C., preferably 60° C., and finally isolating the inactivated microorganisms by concentration and filtration.

This treatment may be carried out also at the beginning of Step iii) of intracellular loading in hypo- or isotonic medium. In this case, emptied microorganisms obtained from Step i) are resuspended in one part of the hypo- or isotonic medium containing the substances to be re-incorporated, and the mixture thus obtained is then heated in the conditions described above. After cooling to 2-8° C., preferably at 4° C., the remaining part of the hypo- or isotonic solution is added, and the step of intracellular loading is then carried out, as described in Step iii).

Inactivation conditions must be such as not to cause alterations in the wall structure of the microorganism, and must be chosen according to the characteristics of resistance of the microorganism itself. Control of the degree of inactivation of the cells of the microorganism at the end of Step ii) is carried out by culture tests on Platecount agar, as here briefly described: a small aliquot of treated micro-organic cells are resuspended in an aliquot of the previously extracted solution, dialysis is then performed and the isotonicity of the solution is re-established, whenever necessary. When the cells have re-acquired their original shape, approximately 1 g or 1 ml of the suspension is inoculated into a selective culture medium (approximately 15-25 ml of culture broth) and incubated (at approx. 37° C. for bacteria; at approx. 25° C. in the case of mycetes) for 3648 hours. Since this first phase may not be sufficient to recover viable microorganisms, seeding may be repeated by further inocula (preferably 3), using the culture broth from the step i). Possible growth processes are checked by analysis of the concentration of the microrganic colonies present by turbidimetric analyses or microscope observation (on a slide after colouring), or by colony count.

In Step iii) one or more of the active agents according to the invention are loaded into the inactivated empty microrganic cells, by incubating said cells in a hypo- or isotonic aqueous solution containing the pharmacologically and/or nutritionally active agents, under gentle stirring, for a time sufficient for the uptake of the active agent into the cells, preferably for a period ranging from 4 hours to 4 days, preferably 16 hours, at a temperature of between 2 and 40° C., preferably at 25° C. The hypotonic aqueous solution preferably comprises:

NaCl in concentrations lower than 0.12 M;

optionally sodium citrate in concentrations lower than 0.025 M;

Preferably, the above-mentioned hypotonic solution comprises NaCl 0.05 M and sodium citrate 0.005 M.

Optionally, a suitable antibacterial agent, such as polyphosphates or para-benzoates may be added.

The isotonic aqueous solution is preferably a 0.9% (w/v) NaCl solution, optionally comprising also low concentrations of sodium citrate ranging from 0.01 to 0.05 M.

Preferably, the isotonic solution according to the invention is a 0.9% NaCl solution comprising 0.025 M sodium citrate.

According to the present invention, the intracellular loading is performed by incubation of the cells in the hypotonic solution comprising the active agent/s which is then absorbed into the microorganisms. NaCl is then continuously added to the solution until isotonicity is reached.

With this treatment, microorganisms re-acquire their original shape. Control of absorption (microorganism loading) can be carried out also by measuring the amount of active agent still present in the aqueous suspension.

According to a further embodiment, when intracellular loading is performed by incubation in isotonic solution, cells are suspended in the isotonic medium comprising the active (agent) or principles; after such incubation emptied cells re-acquire their original shape. Control of absorption is carried out by checking the amount of active agent still present in the isotonic aqueous suspension.

According to another embodiment, the emptying in Step i) is carried out by incubating the cells in a hypertonic solution of the active agent itself. In this case, a pharmacologically or nutritionally active agent according to the invention is prepared in a hypertonic form. The hypertonic solution of the active agent is added, optionally in the presence of sodium citrate, to the solution comprising microorganisms, and emptying-out of the endocellular component from the cell (microorganism) is obtained.

At this point, after optional chemico-physical inactivation of the microorganisms (Step ii), the hypertonic solution is diluted to values of hypo- or isotonicity (Step iii), thus allowing the active agent to enter into the cell and the latter to recover its shape.

The advantage of this alternative procedure lies in that all the operations are carried out in one and the same medium and container.

The efficiency of loading is good and equivalent according to both embodiments. According to a further embodiment, introduction of the active agent into the microorganism is performed in the presence of an isotonic solution, according to the following steps:

1) the microorganism is inactivated by thermal route, for example at 60-65° C. for 30-120 min, preferably at 65° C. for 30 min;

2) inactivated cells are re-suspended in NaCl isotonic medium containing the active principle to be incorporated;

3) the suspension is left under stirring for 48-72 hours in the same conditions as set out for the other examples; and 4) the suspension is centrifuged, as previously described.

Once loading of the active agent into the cell is completed, according to the processes of the present invention, it is possible to add a buffer solution containing a stabilizer for the cells (which acts by stabilizing the membrane pores), or a fixing agent and hence to stop or limit leakage of the active agent from the cell.

The buffer used may be a suspension or a solution comprising, for example, a fixing agent such as formaldehyde or glutaraldehyde.

Alternatively, stabilization of the cell membrane pores may be carried out by thermal treatment (at 60-65° C. for 30-120 min, preferably 60 min).

Finally, the microorganisms obtained from Step iii) may be concentrated, preferably by filtration, to a small volume of hypo- or isotonic medium, or also may be used directly for administration or for the preparation of foodstuff compositions, or also may be separated by centrifugation from the medium.

Alternatively, the microorganisms can be separated from the culture medium by filtration or centrifugation, and the supernatant recovered. The supernatant is then concentrated, and in case the active agent is a protein, it can be recovered by saline precipitation with ammonium sulphate, as described by Robert K. Scopes in "Protein Purification, Principles and Practice", Chap. 3, Pages 39-52, Springer-Verlag New York Inc., 1982. The protein precipitate can then be separated by filtration, re-suspended in water and dialysed against water with membranes of suitable molecular cut-off (i.e. 2 000/5 000 daltons), for 48 hours, operating at cold temperatures.

The loaded microorganisms are then ready for use in foodstuff preparation or in animal feed. At the intestinal level, the microorganism cell walls are lysed and the active agents incorporated therein are then released. The protected active agents maintain their original properties unaltered, as they do not get in contact with intestinal de-activating factors.

A further object of the present invention is the use of the above-mentioned inactivated microorganisms containing active agents, in the field of foodstuff for human consumption and/or for animal feeding, preferably in zootechnics, namely in the rearing of livestock.

Finally, a further object of the present invention is represented by food compositions, for both human and animal alimentation, comprising inactivated microorganisms enriched with one or different active agents prepared according to the present invention, in association with conventional foodstuffs or animal feed, and possibly in the presence of appropriate excipients and/or diluents. The quantity of microorganisms to be administered varies according to the animal species treated, the diet followed, the general state of health of the animal, and the conditions of rearing, and preferably ranges from 0.1 to 20 g/kg of animal feed, and from 0.1 to 5 g/day for humans. For poultry, the microorganisms of the invention are preferably administered in a quantity of between 30 and 70 mg/day. The above-mentioned compositions are preferably used in the livestock-rearing sector, in the form of premixes or feed. In fact, the cell walls of the microorganisms are able to protect the characteristics of structure and activity of the active agents contained therein, both in the phase of preparation of the mixture and during its passage through the gastric tract.

It has been found that the active agents inserted into the microorganisms according to the invention are in particular, stable to changes in temperature, and consequently they are particularly suitable for preparations that require heating of the composition. This is important, for example, when the active agent is mixed with foodstuff or animal feed, or when the food mixture is heated or boiled before ingestion by humans or by animals.

In particular, as described in Example 5, it has been found that the ascorbic acid contained in the microorganism prepared according to the invention is thermostable even at 120° C., whereas it is known from the literature that ascorbic acid as such is easily denatured at much lower temperatures.

EXPERIMENTAL PART

The present invention will now be described with reference to particular embodiments in the examples that follow.

Example 1

Yeasts Modified by Incorporation of Ascorbic Acid

In this assay, yeasts are partially emptied with a hypertonic NaCl solution and loaded with an isotonic ascorbic acid solution.

Step I)—30 g of commercially available yeast paste of Saccharomyces cerevisiae (containing 10 g of dry yeast) were resuspended in 170 g of a hypertonic solution of NaCl 2.0M (116.88 g/l of sodium chloride and 29.41 g/l of trisodium citrate.$2H_2O$) and kept at 25° C. for 6 hours under gentle stirring.

Step II)—The cells were already inactivated by the hypertonic treatment of Step I), and consequently a further inactivation by means of chemico-physical systems was not required.

Step III)—From the suspension obtained in Step I), an aliquot of 80 g was taken, and this was centrifuged at 4000 r.p.m. (1252 R.C.F.) for 15 minutes. The centrifugate obtained was washed with 80 ml of an isotonic solution of ascorbic acid (59.4 g/l), and the cells were recovered and brought back up to 80 g with an isotonic solution of ascorbic acid.

The suspension was kept for 6 hours at 25° C. under gentle stirring.

The cells obtained may be stored up to the moment of use or may be analytically tested for the quantity of ascorbic acid incorporated.

Analytical Test of the Suspensions Obtained

The suspensions obtained as described above were tested in order to check the quantity of ascorbic acid that had accumulated in the cells.

Step IV)—The suspension obtained in Step III) was centrifuged at 4000 r.p.m. (1252 R.C.F.). The precipitated was washed twice (sample A) or thrice (sample B) with an isotonic solution of sodium chloride (0.9%) keeping it in suspension during each washing.

Step V)—The centrifugate was brought up to 80 g with the hypertonic solution (NaCl 2.0M) used for Step I). In order to complete the osmotic treatment, the suspension was kept under gentle stirring for 6 hours at 25° C.

Step VI)—The ascorbic acid present in each solution (mg/ml) and in the microorganism (mg/g) was determined by HPLC, by the use of the following formula:

$$mg/g = A_c \times P_s \times f_s \times D_s \times 1000 / A_s \times P_c \times D_c,$$

where:

$A_c$=Sample Absorbance
$P_s$=Standard weight
$f_s$=Standard factor
$D_s$=Standard dilution
$A_s$=Standard absorbance
$P_c$=Sample weight
$D_c$=Sample dilution Step VII)—Determination of Cell Viability A small part (1 g) of the centrifugate obtained in Step IV) was then used to ascertain the viability of the cells, using the microbiological technique of fermentation of saccharose in a 9.25% isotonic solution and counting of the viable microorganisms on Platecount agar. The Total Viable Cells (TVC) method was used, which is commonly known and described in microbiology manuals, such as Berkley's Manual, and Trattato di Microbiologia, Davis and Dulbecco, Piccin Ed., Padova. The results presented in table corresponding to Step VI show that no viable cells could be detected after 24 hours of growth, indicating that the microorganisms have been inactivated by the previous treatment in hypertonic solution.

Test 2NC-A, B
Step I Treatment with hypertonic solution

| Test | S. cerevisiae Weight [g]* | Hypertonic solution | NaCl concentr. [%] | time [hours] | temperature [° C.] |
|---|---|---|---|---|---|
| 2NC-A | 15.00 | 185.00 | 11.69 | 6 | 25 |
| 2NC-B | 15.00 | 185.00 | 11.69 | 6 | 25 |

*Weighing carried out on substance as such, loss due to drying 63.40%

Step II Treatment with isotonic solution of ascorbic acid

| Test | Centrifugate Weight [g] | Washed w.isotonic soln [g] | centrifugate Weight [g] | isot. Soln. added Weight [g] | Time [hours] | Temperature [° C.] |
|---|---|---|---|---|---|---|
| 2NC-A | 9.51 | 70.49 | 13.05 | 66.95 | 6 | 25 |
| 2NC-B | 9.63 | 70.37 | 13.01 | 66.99 | 6 | 25 |

Step III Washing with NaCl (0.9%) isotonic solution

| Test | centrifugate Weight [g] | washed 1X with isot. soln Weight [g] | centrifugate Weight [g] | washed 2X with isot. soln Weight [g] | centrifugate Weight [g] | washed 3X isot. soln Weight [g] |
|---|---|---|---|---|---|---|
| 2NC-A | 10.67 | 69.33 | 11.06 | 68.94 | 10.93 | |
| 2NC-B | 10.79 | 69.21 | 11.15 | 68.85 | 11.10 | 68.90 |

Step IV Treatment with hypertonic solution to release the incorporated ascorbate

| Test | centrifugate Weight [g] | Hypertonic soln added | centrifugate Weight [g] | time [hours] | temperature [° C.] |
|---|---|---|---|---|---|
| 2NC-A | 10.93 | 69.07 | 9.05 | 6 | 25 |
| 2NC-B | 10.95 | 69.05 | 8.97 | 6 | 25 |

Step V Incorporated ascorbic acid as measured by HPLC
HPLC data

| Batch | 2NC-A | 2NC-B |
|---|---|---|
| Ac | 3373.79 | 2964.39 |
| Ps | 59.4 | 59.4 |
| Fs | 1 | 1 |
| Ds | 0.0005 | 0.0005 |
| As | 2488.52 | 2488.52 |
| Pc | 4000 | 4000 |
| Dc | 0.011842 | 0.011842 |

$$\%_0(mg/g) = \frac{Ac \times Ps \times fs \times Ds \times 1000}{As \times Pc \times Dc}$$

Incorporated Ascorbic acid

| Ascorbic acid | A | B |
|---|---|---|
| mg/g* | 0.850 | 0.747 |

*The amount of ascorbic acid released by 1 g of yeast over dry matter by osmotic treatment is highlighted in bold type.

Step VI Results of biological activity

| Test | fermentat. of saccharose* after 24 h |
|---|---|
| A, B | negative |

*Saccharose concentration 9.25% (isotonic)

Example 2

Yeasts Modified by Incorporation of Oxytetracycline

The same experiment performed in example 1, was repeated loading yeasts cells with oxytetracycline.

Step I)—30 g of commercially available yeast paste of *Saccharomyces cerevisiae* (containing 10 g of dry yeast) were suspended in 170 g of a hypertonic solution of NaCl 2.0M (116.88 g/l of sodium chloride and 29.41 g/l of sodium citrate 2H$_2$O) and kept at 25° C. for 6 hours under gentle stirring.

Step II)—The cells were already inactivated by the hypertonic treatment of Step I), and consequently a further inactivation by means of chemico-physical systems was not required.

Step III)—From the suspension obtained in Step I), an aliquot of 80 g was taken, this was centrifuged at 4000 r.p.m. (1252 R.C.F.) for 15 minutes. The centrifugate obtained was washed with 80 ml of an isotonic solution of oxytetracycline HCl (32.6 g/l) and citric acid (27.6 g/l), and the cells were recovered and brought back up to 80 g with an isotonic solution as above. The suspensions were kept for 6 hours at 25° C. under gentle stirring.

The cells obtained may be stored up to the moment of use or may be analytically tested for the quantity of oxytetracycline loaded.

Analytical Test of the Suspensions Obtained

The suspension obtained as described above was tested in order to check the quantity of oxytetracycline that had accumulated in the cells.

Step IV)—The suspension obtained in Step II) was centrifuged at 4000 r.p.m. (1252 R.C.F.). The centrifugate was washed twice (A) or thrice (B) with an isotonic solution of sodium chloride (0.9%) keeping it in suspension for 10 minutes before centrifugation.

Step V)—The centrifugate was brought up to 80 g with the hypertonic solution (NaCl 2.0M) used for Step I). In order to complete the osmotic treatment, the suspension was kept under gentle stirring for 6 hours at 25° C.

Step VI)—The oxytetracycline HCl present in each solution (mg/ml) and in the microorganism (mg/g) was determined by HPLC, by the use of the following formula:

$$mg/g = A_c \times P_s \times f_s \times D_s \times 1000 / A_s \times P_c \times D_c,$$

where:

$A_c$=Sample Absorbance $P_s$=Standard weight $f_s$=Standard factor $D_s$=Standard dilution $A_s$=Standard absorbance $P_c$=Sample weight $D_c$=Sample dilution Step VII)—Determination of Cell Viability A small part (1 g) of the centrifugate obtained in Step IV) was then used to ascertain the vitality of the cells, using the microbiological technique of fermentation of saccharose in a 9.25% isotonic solution and counting of the vital germs with Platecount agar. The results presented in table corresponding to Step VII show that no viable cells could be detected after 24 hours of growth, indicating that the microorganisms have been inactivated by the previous treatment in hypertonic solution.

Test 3NO-A, B
Step I Treatment with hypertonic solution

| Test | S. cerevisiae Weight [g]* | hypertonic solution Weight [g] | NaCl concentr. [%] | time [hours] | temperature [° C.] |
|---|---|---|---|---|---|
| A, B | 30.00 | 170.00 | 11.69 | 6 | 25 |

*Loss due to drying 63.40%

Step III Treatment with isotonic solution containing oxytetracycline HCl and citric acid

| Test | Centrifugate Weight [g] | washed with oxytetracycl. Weight [g]* | Centrifugate Weight [g] | oxytetracycl. added Weight [g] | time [hours] | Temp. [°C.] |
|---|---|---|---|---|---|---|
| 3NO-A | 9.34 | 70.66 | 13.07 | 66.93 | 6 | 25 |
| 3NO-B | 9.27 | 70.73 | 13.22 | 66.76 | 6 | 25 |

* isotonic solution containing 3.26% of oxytetracycline HCl and 2.76% of citric acid Step IV Washing with NaCl (0.9%) isotonic solution

| Test | centrifugate Weight [g] | 1X washing. NaCl soln Weight [g] | Centrifugate Weight [g] | 2X washings NaCl soln Weight [g] | centrifugate Weight [g] | 3X washings NaCl soln Weight [g] |
|---|---|---|---|---|---|---|
| 3NO-A | 14.40 | 65.60 | 13.79 | 66.21 | 13.10 | |
| 3NO-B | 14.54 | 65.46 | 14.10 | 65.90 | 13.45 | 66.55 |

Step V Hypertonic solution treatment

| Test | centrifugate Weight [g] | hypertonic solution ad Weight [g] | centrifugate Weight [g] | time [hours] | Temp. [° C.] |
|---|---|---|---|---|---|
| 3NO-A | 13.10 | 66.99 | 9.05 | 6 | 25 |
| 3NO-B | 13.55 | 66.45 | 8.97 | 6 | 25 |

Step VI Incorporated Oxytetracyclin as measured by HPLC
HPLC data

| Batch | 3NO-A | 3NO-B |
|---|---|---|
| Ac | 3309.00 | 3180.09 |
| Ps | 32.6 | 32.6 |
| Fs | 1 | 1 |
| Ds | 0.001 | 0.001 |
| As | 480.63 | 480.63 |
| Pc | 4000 | 4000 |
| Dc | 0.118 | 0.118 |

$$\%_0 (mg/g) = \frac{Ac \times Ps \times fs \times Ds \times 1000}{As \times Pc \times Dc}$$

| Incorporated oxytetracyclin | | | | |
|---|---|---|---|---|
| | Oxytetracyclin | | final soln. | |
| washings | mg/ml | 0.249 | 2.363 | 0.920 |
| A | mg/g *) | 4.738 | | |
| B | mg/g *) | 4.554 | | |

*) The amount of oxytetracycline released by 1 g of yeast over dry matter by osmotic treatment is highlighted in bold type.

| Step VII Results of biological activity | |
|---|---|
| Test | fermentat. of saccharose* after 24 h |
| A, B | negative |

*Saccharose concentration 9.25% (isotonic)

Example 3

Yeasts Modified by Incorporation of Sodium Sulphadimethoxine

Yeast cells have been emptied by hypertonic solution treatment and then loaded with an isotonic sodium sulphadimethoxine solution.

Step I)—30 g of commercially available yeast paste of *Saccharomyces cerevisiae* (containing 10 g of dry yeast) were suspended in 170 g of a hypertonic solution of NaCl 2.0M (116.88 g/l of sodium chloride and 29.41 g/l of sodium citrate 2H₂O) and kept at 25° C. for 6 hours under gentle stirring.

Step II)—The cells were already inactivated by the hypertonic treatment of Step I), and consequently a further inactivation by means of chemico-physical systems was not required.

Step III)—From the suspension obtained in Step I), an aliquot of 80 g was taken, and this was centrifuged at 4000 r.p.m. (1252 R.C.F.) for 15 minutes. The centrifugate obtained was washed with 80 ml of an isotonic solution of sodium sulphadimethoxine (51.7 g/l), and the cells were recovered and brought back up to 80 g with an isotonic solution of sodium sulphadimethoxine and sodium citrate 0.025M. The suspension was kept for 6 hours at 25° C. under gentle stirring. The cells obtained may be stored up to the moment of use or may be tested for the quantity of sulphadimethoxine that has been loaded.

Analytical Test of the Suspensions Obtained

The suspension obtained as described above was tested in order to check the quantity of sodium sulphadimethoxine that had accumulated in the cells.

Step IV)—The suspension obtained in Step II) was centrifuged at 4000 r.p.m. (1252 R.C.F.). The centrifugate was washed twice (A) or thrice (B) with an isotonic solution of sodium chloride (0.9%) keeping it in suspension for 10 minutes before centrifugation.

Step V)—The centrifugate was brought up to 80 g with the hypertonic solution (NaCl 2.0M) used for Step I). In order to complete the osmotic treatment, the suspension was kept under gentle stirring for 6 hours at 25° C.

Step VI)—The sodium sulphadimethoxine present in each (mg/ml) and in the microorganism (mg/g) was determined by HPLC, by the use of the following formula:

$$mg/g = A_c \times P_s \times f_s \times D_s \times 1000 / A_s \times P_c \times D_c,$$

where:

$A_c$=Sample Absorbance
$P_s$=Standard weight
$f_s$=Standard factor
$D_s$=Standard dilution
$A_s$=Standard absorbance
$P_c$=Sample weight
$D_c$=Sample dilution Step VII)—Determination of Cell Viability.

A small part (1 g) of the centrifugate obtained in Step IV) was then used to ascertain the vitality of the cells, using the microbiological technique of fermentation of saccharose in a 9.25% isotonic solution and counting of the vital microorganisms (C.F.U.) with Platecount agar. The results presented in table corresponding to Step VII show that no viable cells could be detected after 24 hours of growth, indicating that the microorganisms have been inactivated by the previous treatment in hypertonic solution.

Test 4NS1-A, B

Step I Treatment with hypertonic solution

| Test | yeast S. cerevisiae Weight [g]* | hypertonic solution Weight [g] | NaCl concentr. [%] | time [hours] | temperature [° C.] |
|---|---|---|---|---|---|
| A, B | 30.00 | 170.00 | 11.69 | 6 | 25 |

*Weighing carried out on substance as such, loss due to drying: 63.40%

Step III Treatment with sodium sulphadimethoxine isotonic solution

| Test | centrifugate Weight [g] | Isotonic soln. wash Weight [g] | centrifugate Weight [g] | Isotonic soln. added Weight [g] | time [hours] | temperature [°C.] |
|---|---|---|---|---|---|---|
| 4NS1-A | 9.62 | 70.38 | 12.42 | 67.58 | 6 | 25 |
| 4NS1-B | 9.64 | 70.36 | 12.50 | 67.50 | 6 | 25 |

Step IV Washing with NaCl (0.9%) isotonic solution

| Test | centrifugate Weight [g] | 1X washing Weight [g] | centrifugate Weight [g] | 2X washing Weight [g] | centrifugate Weight [g] | 3X washing Weight [g] |
|---|---|---|---|---|---|---|
| 4NS1-A | 13.57 | 66.43 | 13.32 | 66.68 | 13.25 | |
| 4NS1-B | 13.41 | 66.59 | 13.27 | 66.73 | 13.19 | 66.81 |

| | | Step V Treatment with hypertonic solution to release loaded sulphadimethoxine | | | |
|---|---|---|---|---|---|
| Test | centrifugate Weight [g] | hypertonic solution Weight [g] | centrifugate Weight [g] | time [hours] | Temperature [° C.] |
| 4NS1-A | 13.25 | 66.75 | 9.92 | 6 | 25 |
| 4NS1-B | 12.69 | 67.31 | 10.06 | 6 | 25 |

| Step VI Incorporated sulphadimetoxin as measured by HPLC HPLC data | | |
|---|---|---|
| Batch | 4NS1-A | 4NS1-B |
| Ac | 2266.98 | 1830.04 |
| Ps | 51.7 | 51.7 |
| Fs | 1 | 1 |
| Ds | 0.001 | 0.001 |
| As | 1741.13 | 1741.13 |
| Pc | 4000 | 4000 |
| Dc | 0.0118 | 0.0118 |

$$\%_0(mg/g) = \frac{Ac \times Ps \times fs \times Ds \times 1000}{As \times Pc \times Dc}$$

| Incorporated sulphadimetoxin | | | | | |
|---|---|---|---|---|---|
| washings | mg/ml | 0.075 | 4.440 | 0.424 | |
| A | mg/g* | 1.421 | | | |
| B | mg/g* | 1.147 | | | |

*The amount of sulphadimetoxine released by 1 g of yeast over dry matter by osmotic treatment is highlighted in bold type.

| Step VII Results of biological activity | |
|---|---|
| Test | fermentat. of saccharose* after 24 h |
| A, B | negative |

*Saccharose concentration 9.25% (isotonic)

Example 4

Yeasts Modified by Incorporation of Sodium Sulphadimethoxin (Hypertonicity Due to the Drug)

In this example is shown that is possible to induce the hypertonic shock by an hypertonic solution of the sodium salt of the drug itself.

Step I)—To 30 g of commercially available yeast paste of *Saccharomyces cerevisiae* (containing 20 g of water) were added 3.32 g of sodium sulphadimethoxin, 0.29 g of sodium citrate.2H$_2$O and 8.5 g of water under gentle stirring. The suspension obtained was kept at 25° C. for 6 hours.

Step II)—The cells were already inactivated by the hypertonic solution treatment, and consequently further inactivation by means of chemico-physical systems was not required.

Step III)—The suspension obtained in Step I) was diluted with 30.61 g of distilled water at isotonicity, and the suspension was kept under gentle stirring for 6 hours at 25° C.

The cells obtained may be stored up to the moment use or tested for the quantity of sulphadimethoxin that has penetrated into them.

Analytical Test of the Suspension Obtained

The suspension as previously obtained was tested to ascertain the quantity of sodium sulphadimethoxin that had accumulated in the cells.

Step IV)—For analytical reasons, the suspension obtained in Step III) was diluted with an isotonic solution of sodium sulphadimethoxin (5.17%) to 200 g. An aliquot of 80 g of suspension was taken. The suspension was centrifuged at 10 000 r.p.m., and the centrifugate was washed twice (A) or thrice (B) with an isotonic solution of sodium chloride (0.9%). The suspension was stirred for 10 minutes before each washing.

Step V)—The centrifugate was brought to 80 g with a hypertonic solution of NaCl 2.0M (116.88 g/l of sodium chloride and 29.41 g/l of sodium citrate 2H$_2$O) under gentle stirring for 6 hours at 25° C.

Step VI)—The sodium sulphadimethoxin present in solution (mg/ml) and in the microorganism (mg/g) was determined by HPLC, by the use of the following formula:

$$mg/g = A_c \times P_s \times f_s \times D_s \times 1000 / A_s \times P_c \times D_c,$$

where:
$A_c$=Sample Absorbance
$P_s$=Standard weight
$f_s$=Standard factor
$D_s$=Standard dilution
$A_s$=Standard absorbance
$P_c$=Sample weight
$D_c$=Sample dilution The values obtained were similar to those obtained in the previous example.

Step VII)—Determination of Cell Viability

A small part (1 g) of the centrifugate obtained in Step IV) was then used to ascertain viability of the cells, using the microbiological technique of fermentation of saccharose in a 9.25% isotonic solution and counting of the vital germs with Platecount agar. The results presented in table corresponding to Step VII show that no viable cells could be detected after 24 hours of growth, indicating that the microorganisms have been inactivated by the previous treatment in hypertonic solution.

| Test 6NS1-A,B Step I Treatment with hypertonic solution of sodium sulphadimethoxin ||||||||
| --- | --- | --- | --- | --- | --- | --- | --- |
| Test | strain S. cerevisiae Weight [g]* | sulphadim. added Weight [g] | Na-citrate added Weight [g] | water added Weight [g] | sulphadim. concentration [%] | time [hours] | temperature [° C.] |
| A, B | 30.00 | 3.32 | 0.29 | 8.50 | 10.34 | 6 | 25 |

*Weighing carried out on the substance as such (containing 10 g of dry yeast and 20 g of water)

| Step III Treatment with isotonic solution of sodium sulphadimethoxin ||||| 
| --- | --- | --- | --- | --- |
| Test | water added Weight [g] | sulphadim. concentr. [%] | Time [hours] | Temperature [° C.] |
| A, B | 30.61 | 5.17 | 6 | 25 |

| Step IV Washing with NaCl (0.9%) isotonic solution |||||||
| --- | --- | --- | --- | --- | --- | --- |
| Test | centrifugate Weight [g] | 1X washing Weight [g] | centrifugate Weight [g] | 2X washing Weight [g] | centrifugate Weight [g] | 3X washing Weight [g] |
| 6NS1-A | 16.25 | 63.75 | 15.81 | 64.19 | 15.99 | |
| 6NS1-B | 16.20 | 63.80 | 15.21 | 64.79 | 15.41 | 64.59 |

| Step V Treatment with hypertonic solution(*) to release the sulphadimethoxin incorporated in the cells ||||||
| --- | --- | --- | --- | --- | --- |
| Test | centrifugate Weight [g] | hypertonic solution* Weight [g] | time [hours] | Temperature [° C.] | centrifugate Weight [g] |
| 6NS1-A | 15.99 | 64.01 | 6 | 25 | 11.81 |
| 6NS1-B | 15.47 | 64.53 | 6 | 25 | 11.22 |

*hypertonic solution (116.88 g/l of sodium chloride and 29.41 g/l of sodium citrate $2H_2O$)

| Step VI Incorporated sulphadimethoxin as measured by HPLC HPLC data |||
| --- | --- | --- |
| Batch | 6NS1-A | 6NS1-B |
| Ac | 2049.23 | 1908.71 |
| Ps | 51.7 | 51.7 |
| Es | 1 | 1 |
| Ds | 0.001 | 0.001 |
| As | 1782.36 | 1782.36 |
| Pc | 4000 | 4000 |
| Dc | 0.0118 | 0.0118 |

$$\%_0(mg/g) = \frac{Ac \times Ps \times fs \times Ds \times 1000}{As \times Pc \times Dc}$$

| Sulphadimetoxin final soln. |||||
| --- | --- | --- | --- | --- |
| washings | mg/ml | 0.066 | 3.741 | 0.275 |
| A | mg/g* | 1.255 | | |
| B | mg/g* | 1.169 | | |

*The quantity of sulphadimethoxin released by 1 g of yeast over dry matter by osmotic treatment is highlighted in bold type.

| Step VII Residual biological activity ||
| --- | --- |
| Test | fermentat. of saccharose* after 24 h |
| A, B | negative |

*Saccharose concentration 9.25% (isotonic)

Example 5

Yeasts Modified by Incorporation of Ascorbic Acid Followed by Thermal Stabilization The incorporation was repeated as in Example 1, with in addition thermal stabilization of the modified yeast.

Step I)—30 g of commercially available yeast paste of Saccharomyces cerevisiae (corresponding to 10 g of dried yeast) was suspended in 170 g of a hypertonic solution of NaCl 2.0M (116.88 g/l of sodium chloride and 29.41 g/l of sodium citrate $2H_2O$) and kept at 25° C. for 6 hours under gentle stirring.

Step II)—The cells were already inactivated by the hypertonic treatment of Step I), and consequently a further inactivation by means of chemico-physical systems was not required.

Step III)—From the suspension obtained in Step I), an aliquot of 80 g was taken, and this was centrifuged at 4000 r.p.m. (1252 R.C.F.) for 15 minutes. The centrifugate obtained was washed with 80 ml of an ascorbic acid isotonic solution (59.4 g/l), and cells were recovered and brought back up to 80 g with the same isotonic solution.

The suspension was kept for 6 hours at 25° C. under gentle stirring.

The cells obtained may be stored up to the moment of use or may be tested for the quantity of ascorbic acid that has penetrated into them.

Analytical Test of the Suspension Obtained

The suspension obtained as described above was tested in order to check the quantity of ascorbic acid that had been loaded in the cells.

Step IV)—The suspension obtained in Step III) was centrifuged at 4 000 r.p.m. (1252 R.C.F.). The centrifugate was washed twice with an isotonic solution of sodium chloride (0.9%) keeping it in suspension for 10 minutes before centrifugation. The centrifugate was vacuum-dried on silica gel at room temperature (A).

Step V)—The dried yeast was either used as such (A) or an aliquot (1 g) heated for 15 minutes at 120° C. (B). Both fraction were treated with 10 ml of a hypertonic solution as in Step I). To complete the osmotic treatment, the suspension was kept under gentle stirring for 6 hours at 25° C.

Step VI)—The ascorbic acid present in the washing solution (mg/ml) and in the microorganism (mg/g) was determined by HPLC, by the use of the following formula:

$$mg/g = A_c \times P_s \times f_s \times D_s \times 1000 / A_s \times P_c \times D_c,$$

where:

$A_c$=Sample Absorbance $P_s$=Standard weight $f_s$=Standard factor $D_s$=Standard dilution $A_s$=Standard absorbance $P_c$=Sample weight $D_c$=Sample dilution Step VII)—Determination of Cell Viability A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VII show that no viable cells could be detected after 24 hours of growth, indicating that the microorganisms have been inactivated by the previous treatment in hypertonic solution.

Test 5NC-A, B
Step I Treatment with hypertonic solution

| Test | S. cerevisiae Weight [g]* | hypertonic solution Weight [g] | NaCl concentr. [%] | time [hours] | temperature [° C.] |
|---|---|---|---|---|---|
| A, B | 15.00 | 185.00 | 11.69 | 6 | 25 |

*Weighing carried out on substance as such

Step III Treatment with isotonic solution of ascorbic acid

| Test | Centrifugate Weight [g] | washing with isotonic soln. Weight [g] | Isotonic Centrifugate Weight [g] | soln. added Weight [g] | time [hours] | Temperature [° C.] |
|---|---|---|---|---|---|---|
| 5NC | 9.52 | 70.48 | 12.81 | 67.19 | 6 | 25 |

Step IV Washing with NaCl (0.9%)isotonic solution and drying

| Test | centrifugate Weight [g] | 1X wash NaCl 0.9% Weight [g] | centrifugate Weight [g] | 2X wash NaCl 0.9% Weight [g] | centrifugate Weight [g] | Dry yeast Weight [g] * |
|---|---|---|---|---|---|---|
| 5NC | 10.66 | 69.14 | 10.77 | 69.23 | 10.85 | 2.81 |

* Loss due to transfer into drying capsule

Step V
Treatment with hypertonic solution to release incorporated ascorbate

| Test | Dry yeast Weight [g] | Hypertonic Soln. Weight [g] | time [hours] | Temperature [° C.] |
|---|---|---|---|---|
| A | 1.17 | 11.17 | 6 | 25 |
| B | 1.00 | 11.00 | | |

Step VI Incorporated ascorbic acid as measured by HPLC
HPLC data

| Batch | 5NC-A | 5NC-B |
|---|---|---|
| Ac | 7760.00 | 6305.3 |
| Ps | 59.4 | 59.4 |
| Fs | 1 | 1 |
| Ds | 0.0005 | 0.0005 |
| As | 3182.27 | 3182.27 |
| Pc | 1170 | 1000 |
| Dc | 0.045 | 0.045 |

$$\%_0 (mg/g) = \frac{Ac \times Ps \times fs \times Ds \times 1000}{As \times Pc \times Dc}$$

Incorporated ascorbic acid

| | Ascorbic acid | | final soln. | |
|---|---|---|---|---|
| washings | mg/ml | 0.16 | 1.452 | 0.147 |
| A | mg/g * | 1.376 | | |
| B | mg/g * | 1.308 | | |

* The quantity of ascorbic acid released by 1 g of yeast over dry matter by osmotic treatment is highlighted in bold type.

Step VII Results of biological activity

| Test | fermentat. of saccharose* after 24 h |
|---|---|
| A, B | negative |

*Saccharose concentration 9.25% (isotonic)

Example 6

Yeasts Modified by Incorporation of Ascorbic Acid in Isotonic Solution

Step I) 30 g of yeast paste as in Example 5 were dissolved in an aqueous solution, and the yeast was inactivated by thermal treatment, at 65° C. for 30 minutes.

Step II) The inactivated cells were re-suspended in NaCl 0.9% isotonic solution (80 ml) comprising the ascorbic acid (59.4 g/l) to be incorporated.

Step III) The suspension was left under stirring for 60 hours in the same conditions as for the previous examples.

Step IV) Finally, centrifugation was carried out, as in the previous examples.

Step V) The product was buffered with a 1% glutaraldehyde solution, as stabilizer for the cells, and thus to stop and limit the leakage of the ascorbic acid from the cells.

| Test 6NC Ascorbic acid quantity as measured by HPLC | | |
|---|---|---|
| Ascorbic acid | final soln. | washings |
| mg/ml | 0.038 | 3.124 |
| mg/g * | 0.717 | |

* The quantity of ascorbic acid released by 1 g of yeast over dry matter by osmotic treatment is highlighted in bold type.

| Results of biological activity | |
|---|---|
| Test | fermentat. of saccharose* after 24 h |
| | negative |

Example 7

Microorganism Modified by Incorporation of Zinc

In this treatment yeast cells have been partially emptied by the hypertonic solution, comprising NaCl and Trisodium citrate bihydrate, as already described. Zinc was then incorporated by incubation in a ZnSO₄ isotonic solution. The quantity of zinc loaded into the cells, was measured by Atomic Absorbance Spectrometry (AAS).

Step I)—1680 g of commercially available yeast paste of *Saccharomyces cerevisiae* (corresponding to 560 g of dried yeast) was suspended in 5 600 g of a hypertonic solution of NaCl 1.0M (58.44 g/l of sodium chloride and 9.8 g/l of sodium citrate $2H_2O$) and kept at 25° C. for 16 hours under gentle stirring.

Step II)—The cells were already inactivated by the hypertonic treatment of Step I), and consequently a further inactivation by means of chemico-physical systems was not required.

Step III)—The cellular suspension was centrifuged at 4500 r.p.m. (4596 RCF) for 15 minutes. The centrifugate obtained was washed once with 5.6 L zinc hypotonic solution (80% isotonic) and then with 5.6 L isotonic Zn solution ($ZnSO_4 \cdot H2O$ 45.2 g/l).

The suspension was kept for 6 hours at 25° C. under gentle stirring.

Analytical Test of the Suspension Obtained

The suspension obtained as described above was fixed with formaldehyde as follows: 28 g of 37% formaldehyde were added to the suspension and stirred for 2 hours at 20-25° C. The suspension was then centrifuged and the centrifugate was washed twice with 5.6 L NaCl isotonic solution (0.9%).

Step IV)—The centrifugate was air-dried at 45° C. for 36 hours. After mincing the dried pellets were sifted on a 400μ net.

Step V)—The incorporated zinc quantity was determined by AAS after 5N HCl extraction for two hours at 25° C. under gentle stirring.

Step VI)—Determination of Cell Viability

A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VI show that no viable cells could be detected after 24 hours of growth, indicating that the microorganisms have been inactivated by the previous treatment in hypertonic solution

| Step V: Data from AA Spectrum T st 7/5600 AAS data | |
|---|---|
| Batch | 7/5600 |
| Ac | 0.209 |
| Ps | 66.0 |
| Fs | 0.805 |
| Ds | 0.00006 |
| As | 0.239 |
| Pc | 2500 |
| Dc | 0.0008 |

| Incorporated zinc | |
|---|---|
| Measurement unit | ‰ |
| Content | 1.39 |
| Yield (g) | 514 |
| Washings No. | 2 |

$$\%_0 (mg/g) = \frac{Ac \times Ps \times fs \times Ds \times 1000}{As \times Pc \times Dc}$$

$A_c$: Sample absorbance
$P_s$: Standard weight
$F_s$: Standard factor
$D_s$: Standard dilution
$A_s$: Standard absorbance $P_c$: Sample weight
$D_c$: Sample weight Step VI Results of biological activity

| Test | fermentat. of saccharose* after 24 h |
|---|---|
|  | negative |

*Saccharose concentration 9.25% (isotonic)

Example 8

Microorganism Modified by Incorporation of Zinc and Cobalt

In this treatment yeast cells have been partially emptied by the hypertonic solution, comprising NaCl and Trisodium citrate bihydrate, as already described. Zinc and cobalt were then incorporated by incubation in a $ZnSO_4$ and $CoSO_4$ hypotonic solution. The quantity of zinc and cobalt loaded into the cells, was measured by Atomic Absorbance Spectrometry (AAS).

Step I)—168 g of commercially available yeast paste of Saccharomyces cerevisiae (corresponding to 56 g of dried yeast) was suspended in 560 g of a hypertonic solution of NaCl 2.0M (58.45 g/l of sodium chloride and 9.80 g/l of trisodium citrate $2H_2O$) and kept at 25° C. for 16 hours under gentle stirring.

Step II)—The cells were already inactivated by the hypertonic treatment of Step I), and consequently a further inactivation by means of chemico-physical systems was not required.

Step III)—The cellular suspension was centrifuged at 4500 r.p.m (4596 RCF) for 15 minutes. The centrifugate obtained was washed twice with 560 g zinc/cobalt hypotonic solution (prepared as follows: $ZnSO_4$ 32.54 g/l, $CoSO_4$ 5.69 g/l). The suspension was resuspended in 560 g of the same solution and kept 16 hours at 25° C. under gentle stirring.

Analytical Test of the Suspension Obtained

The suspension was divided in two aliquots and then either fixed with formaldehyde (37B) or not (37A) as follows: 1.4 g 37% formaldehyde were added (or not) to the suspension and stirred for 2 hours at 20-25° C. The suspensions were then centrifuged and the centrifugates were washed twice with 280 g NaCl isotonic solution (0.9%).

Step IV)—The centrifugate was air-dried at 45° C. for 36 hours. After mincing the dried pellets were sifted on a 400μ net.

Step V)—The incorporated zinc quantity was determined by AAS after 5N HCl extraction for two hours at 25° C. under gentle stirring.

Step VI)—Determination of cell viability

A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VI show that no viable cells could be detected after 24 hours of growth, indicating that the microorganisms have been inactivated by the previous treatment in hypertonic solution Step V: Incorporated zinc and cobalt as measured by AA Spectrum Test 37A and 37B
AAS data

| Batch | Zn 37A/560 | Co 37A/560 | Zn 37B/560 | Co 37B/560 |
|---|---|---|---|---|
| Ac | 0.114 | 0.031 | 0.115 | 0.031 |
| Ps | 66.0 | 49.0 | 66.0 | 49.0 |
| Fs | 0.805 | 0.2085 | 0.805 | 0.2085 |
| Ds | 0.00006 | 0.00025 | 0.00006 | 0.0025 |
| As | 0.193 | 0.049 | 0.193 | 0.049 |
| Pc | 2500 | 2500 | 2500 | 2500 |
| Dc | 0.0008 | 0.008 | 0.0008 | 0.008 |

| Measurement unit | ‰ | ‰ | ‰ | ‰ |
|---|---|---|---|---|
| Content | 0.94 | 0.08 | 0.95 | 0.08 |
| Zn/Co | 11.65 | 1 | 11.76 | 1 |
| Yield (g) | 20.77 | 20.77 | 19.25 | 19.25 |
| Washings No. | 2 | 2 | 2 | 2 |

$$‰_0(mg/g) = \frac{Ac \times Ps \times fs \times Ds \times 1000}{As \times Pc \times Dc}$$

$A_c$: Sample absorbance.
$P_s$: Standard weight
$F_s$: Standard factor
$D_s$: Standard dilution
$A_s$: Standard absorbance
$P_c$: Sample weight
$D_c$: Sample weight

Example 9

Microorganism Modified by Incorporation of Zinc and Cobalt

In this treatment yeast cells have been partially emptied by the hypertonic solution, comprising NaCl and Trisodium citrate bihydrate, as already described. Zinc and cobalt were then incorporated by incubation in a $ZnSO_4$ and $COSO_4$ hypotonic solution. The quantity of zinc and cobalt loaded into the cells, was measured by Atomic Absorbance Spectrometry (AAS).

Step I)—168 g of commercially available yeast paste of *Saccharomyces cerevisiae* (corresponding to 56 g of dried yeast) was suspended in 560 g of a hypertonic solution containing 29.46 g NaCl and 4.94 g trisodium citrate.$2H_2O$) and kept at 25° C. for 16 hours under gentle stirring.

Step II)—The cells were already inactivated by the hypertonic treatment of Step I), and consequently a further inactivation by means of chemico-physical systems was not required.

Step III)—The cellular suspension was centrifuged at 4500 r.p.m. (4596 RCF) for 15 minutes. The centrifugate obtained was washed twice with 560 g zinc/cobalt hypotonic solution containing: 32.54 g $ZnSO_4$, 5.69 g $CoSO_4.7H_2O$. The suspension was resuspended in 560 g of the same solution and kept 16 hours at 25° C. under gentle stirring.

Analytical Test of the Suspension Obtained

The suspension was then centrifuged and the centrifugates were washed twice with 560 g NaCl isotonic solution (0.9%).

Step IV)—The centrifugate was air-dried at 45° C. for 36 hours. After mincing the dried mass of cells was sifted on a 400μ net.

Step V)—The incorporated zinc and cobalt quantities were determined by MS after 5N HCl extraction for two hours at 25° C. under gentle stirring. In this case (test 38) the quantity of Zinc and Cobalt are higher than in the previous test (37A and B) due to a more effective fixing treatment in test 38.

Step VI)—Determination of cell viability

A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VI show that no viable cells could be detected after 24 hours of growth, indicating that the microorganisms have been inactivated by the previous treatment in hypertonic solution Step V: Incorporated zinc and cobalt as measured by AASpectrum
Test 38/560
AAS data

| Batch | Zn 38/560 | Co 38/560 |
|---|---|---|
| Ac | 0.142 | 0.037 |
| Ps | 66.0 | 49.0 |
| Fs | 0.805 | 0.2085 |
| Ds | 0.00006 | 0.00025 |
| As | 0.193 | 0.049 |
| Pc | 2500 | 2500 |
| Dc | 0.0008 | 0.008 |
| Measurement unit | ‰ | ‰ |
| Content | 1.17 | 0.10 |
| Zn/Co | 12.16 | 1 |
| Yield (g) | 42.05 | 42.05 |
| Washings No. | 2 | 2 |

$$\%_0 (mg/g) = \frac{Ac \times Ps \times fs \times Ds \times 1000}{As \times Pc \times Dc}$$

$A_c$ Sample absorbance
$P_s$ Standard weight
$F_s$ Standard factor
$D_s$ Standard dilution
$A_s$ Standard absorbance
$P_c$ Sample weight
$D_c$ Sample weight Step VI Results of biological activity

| Test | fermentat. of saccharose* after 24 h |
|---|---|
| A, B | negative |

*Saccharose concentration 9.25% (isotonic)

Example 10

Microorganism Modified by Incorporation Thiamine, Folic Acid and Cyanocobalamin

In this treatment yeast cells have been partially emptied by the hypertonic solution, comprising NaCl and Trisodium citrate bihydrate, as already described. Vitamins were then incorporated by incubation in a vitamins hypotonic solution (hypotonic=80% isotonicity). The quantity of vitamins loaded into the cells, was measured by HPLC.

Step I)—168 g of commercially available yeast paste of *Saccharomyces cerevisiae* (corresponding to 56 g of dried yeast) was suspended in 560 g of a NaCl hypertonic solution containing 29.46 g of sodium chloride and 4.94 g of trisodium citrate.2H$_2$O, and kept at 25° C. for 16 hours under gentle stirring.

Step II)—The cells were already inactivated by the hypertonic treatment of Step I), and consequently a further inactivation by means of chemico-physical systems was not required.

Step III)—The cellular suspension was centrifuged at 4500 r.p.m. (4596 RCF) for 15 minutes. The centrifugate obtained was washed twice with 560 g of an hypotonic solution (containing: monohydrate tiamin 11.2 g, folic acid 2.8 g and cyanocobalamin 0.28 g). The suspension was resuspended in 560 g of the same solution and kept 16 hours at 25° C. under gentle stirring.

Analytical Test of the Suspension Obtained

The suspension was then centrifuged and the centrifugates was washed twice with 560 g NaCl isotonic solution (0.9%).

Step IV)—The centrifugate was air-dried at 45° C. for 36 hours. After mincing the dried pellets were sifted on a 400μ net.

Step V)—The incorporated vitamins quantities were determined by HPLC after 5N HCl extraction for one hours at 25° C. under gentle stirring and after NaOH 0.05N extraction (one hours at 25° C. under gentle stirring).

Step VI)—Determination of cell viability

A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VI show that no viable cells could be detected after 24 hours of growth, indicating that the microorganisms have been inactivated by the previous treatment in hypertonic solution.

Step VI: Incorporated vitamins as measured by HPLC
HPLC data after HCl extraction

| Batch | Tiamine  | Folic Acid | Cyanocobalamin |
|-------|----------|------------|----------------|
| Ac    | 1547.78  | 0.031      | 19.372         |
| Ps    | 12.2     | 8.5        | 10.2           |
| Fs    | 1.000    | 1.000      | 1.000          |
| Ds    | 0.01     | 0.01       | 0.01           |
| As    | 2492.881 | 1928.788   | 540.606        |
| Pc    | 2000.00  | 2000.00    | 2000.00        |
| Dc    | 0.01     | 0.01       | 0.1            |

Incorporated vitamins (HCl extraction)

| Measurement unit | Tiamine | Folic Acid | Cyanocobalamin |
|------------------|---------|------------|----------------|
| Content ‰ (mg/g) | 3.787   | 0.203      | 0.018          |

HPLC data after NaOH extraction

| Batch | Tiamine  | Folic Acid | Cyanocobalamin |
|-------|----------|------------|----------------|
| Ac    | 1426.71  | 1225.693   | 14.822         |
| Ps    | 12.2     | 8.5        | 10.2           |
| Fs    | 1.000    | 1.000      | 1.000          |
| Ds    | 0.01     | 0.01       | 0.01           |
| As    | 2491.785 | 1956.172   | 540.574        |
| Pc    | 2000.00  | 2000.00    | 2000.00        |
| Dc    | 0.01     | 0.01       | 0.1            |

Incorporated vitamins (NaOH extraction)

| Measurement unit | Tiamine | Folic Acid | Cyanocobalamin |
|------------------|---------|------------|----------------|
| Content ‰ (mg/g) | 3.493   | 2.663      | 0.014          |

$$\%_0 (mg/g) = \frac{Ac \times Ps \times fs \times Ds \times 1000}{As \times Pc \times Dc}$$

$A_c$: Sample absorbance
$P_s$: Standard weight
$F_s$: Standard factor
$D_s$: Standard dilution
$A_s$: Standard absorbance
$P_c$: Sample weight
$D_c$: Sample weight Example 11

Treatment of the Microorganisms with Formaldehyde

Cells obtained from Step II) of each of the Examples 1-10 were treated with formaldehyde.

A suspension was prepared with 10 g of cells per 100 ml of water and was kept under stirring, adding 5 ml of an HCHO solution diluted at 1:10 ml. Stirring was continued for 2 hours, and the cells were washed with water by centrifugation to eliminate the excess HCHO of the non-reacted product.

The treatment carried out on portions of incorporated yeasts obtained from the previous tests enabled an average increase of 15% in the amount of active principle retained inside the cells, by reduction of the leaking amount detectable in the washings for corresponding quantities.

Example 12

Treatment of the Microorganisms with Glutaraldehyde

The cells obtained from Step II) of each of the Examples 1-10 were fixed with glutaraldehyde.

A suspension was prepared with 10 g of treated cells per 100 ml of a NaCl 0.9% solution and was treated with 1 ml of a 1% glutaraldehyde solution, and was left to react for 5 minutes under stirring.

The cells were washed with NaCl 0.9% solution and centrifugated to eliminate the excess non-reacted glutaraldehyde.

The treatment carried out on portions of incorporated yeasts obtained from the previous tests enabled an average increase of 25% in the amount of active principle inside the cells, at the same time reducing the amount detectable in the washings for corresponding quantities.

Example 13

Microorganism Modified by Incorporation of α-Tocopherol Acetate

In this treatment yeast cells have been partially emptied by the hypertonic solution, comprising NaCl and Trisodium citrate bihydrate, as already described. α-tocopherol (vitamin E) was then incorporated by incubation in a vitamin hypotonic solution (hypotonic=80% isotonicity). The quantity of vitamin loaded into the cells, was measured HPLC.

Step I)—168 g of commercially available yeast paste of *Saccharomyces cerevisiae* (corresponding to 56 g of dried yeast) was suspended in 560 g of a hypertonic solution of NaCl containing 58.45 g/l NaCl and 9.80 g/l trisodium citrate.2H$_2$O) and kept at 25° C. for 16 hours under gentle stirring.

Step II)—The cells were already inactivated by the hypertonic treatment of Step I), and consequently a further inactivation by means of chemico-physical systems was not required.

Step III)—The cellular suspension was centrifuged at 4500 r.p.m. (4596 RCF) for 15 minutes. The centrifugate obtained was washed twice with 560 g of an aqueous hypotonic solution containing: α-tocopherol acetate 5.60 g, solubilized in 14 g Polyoxyl 35 Castor Oil (NF XVII pag 1966). After centrifugation, the centrifugate was resuspended in 560 g of the same solution and kept 16 hours at 25° C. under gentle stirring.

Analytical Test of the Suspension Obtained

The suspension was then centrifuged and the centrifugates was washed twice with 560 g NaCl isotonic solution (0.9%) and resupended in the same volume and solution (560 g NaCl isotonic solution 0.9%). 2.8 g formalin 37% was added and the solution was gently stirred for two hours, after which centrifugation was performed. An aliquot of the solution (B), was then washed one more time with a NaCl isotonic solution Step IV)—The centrifugate was air-dried at 40° C. for 36 hours. The dried mass of cells was minced and then sifted on a 400μ net.

Step V)—The incorporated vitamin quantities were determined by HPLC after 5N HCl extraction for one hour at 25° C. under gentle stirring.

Step VI)—Determination of Cell Viability

A small part (1 g) of the centrifugates obtained in Step IV) was used to ascertain the vitality of the cells, using the microbiological technique of fermentation of saccharose in a 9.25% isotonic solution and counting of the viable microorganisms with Platecount agar. The results presented in table corresponding to Step VI show that no viable cells could be detected after 24 hours of growth, indicating that the microorganisms have been inactivated by the previous treatment in hypertonic solution.

Step VI: Incorporated α-tocopherol as measured by HPLC.
Test 43/560
HPLC data

| Batch | A | B |
| --- | --- | --- |
| Ac | 57.601 | 65.224 |
| Ps | 50 | 50 |
| Fs | 1.000 | 1.000 |
| Ds | 0.0025 | 0.0025 |
| As | 642.096 | 642.096 |
| Pc | 1023.6 | 1250.4 |
| Dc | 0.0125 | 0.0125 |

Incorporated α-tocopherol

| Measurement unit | A | B |
| --- | --- | --- |
| Content ‰ (mg/g) | 0.876 | 0.812 |

$$‰(mg/g) = \frac{Ac \times Ps \times fs \times Ds \times 1000}{As \times Pc \times Dc}$$

$A_c$: Sample absorbance
$P_s$: Standard weight
$F_s$: Standard factor
$D_s$: Standard dilution
$A_s$: Standard absorbance
$P_c$: Sample weight
$D_c$: Sample weight Yields of the st p:

| | | |
| --- | --- | --- |
| Drying (g): | A = 42.55 | B = 44.22 |
| Mincing (g): | A = 41.31 | B = 43.67 |
| Loss due to drying: | A = 5.35% | B = 5.54% |

The invention claimed is:

1. A process for the preparation of a *Saccharomyces*' cell wall wherein said cell wall contains one or more pharmacological or nutritional substances soluble in an aqueous solution, comprising the following steps:
   i) drawing out the endocellular mass of a *Saccharomyces* by means of a hypertonic treatment;
   ii) separating the endocellular mass and recovering the *Saccharomyces* cell wall; and
   iii) loading one or more pharmacological or nutritional substances soluble in an aqueous solution into the *Saccharomyces* cell wall recovered in step ii) by incubating said *Saccharomyces*' cell wall in a hypotonic aqueous solution or an iso-tonic aqueous solution, comprising the pharmacological or nutritional substances.

2. The process according to claim 1, comprising a further step of chemical or physical inactivation of the *Saccharomyces*' cell wall obtained in step ii).

3. The process according to claim 1, wherein the *Saccharomyces* in step i) is *Saccharomyces cerevisiae*.

4. The process according to claim 1, wherein said pharmacological substance is selected from the group consisting of antibiotics, anti-inflammatories, antibacterials, antivirals, antifungals, antiparasitic agents and vaccines.

5. The process according to claim 4, wherein said antibiotic is oxytetracycline.

6. The process according to claim 4, wherein said antibacterial is sulphadimethoxin.

7. The process according to claim 1, wherein said nutritional substance is selected from the group consisting of sodium quercetin, catechin, isocatechin, aliphatic polyalcohols, polyphenols, flavans, cyanins and resveratrol.

8. The process according to claim 1, wherein said nutritional substance is selected from the group consisting of cyanocobalamin, folic acid, thiamine, α-tocopherol and ascorbic acid.

9. The process according to claim 1, wherein:
   in step i) the endocellular mass is drawn out by incubating the *Saccharomyces*' in a hypertonic solution of the same pharmacologically active substance that is to be loaded into the *Saccharomyces*; cell wall; and
   in step iii) said pharmacologically active substance is already present in the solution and is loaded into the *Saccharomyces*' cell wall with a change of the osmolarity due to dilution of the solution to hypo-tonicity or iso-tonicity.

10. The process according to claim 1, further comprising a treatment of the *Saccharomyces*' cell wall with a fixative or a disinfecting agent.

11. The process according to claim 1, wherein the hypertonic treatment in step i) is obtained by incubation of the microbial cell with or in a hypertonic solution comprising NaCl in concentrations greater than 0.2 M.

12. The process according to claim 1, wherein said hypotonic treatment in step iii) is obtained by means of a hypotonic solution comprising NaCl in concentrations lower than 0.12M.

13. The process according to claim 1, wherein the isotonic treatment in step iii) is performed by a 0.9% NaCl isotonic solution, optionally comprising 0.025M sodium citrate.

14. The process according to claim 13, wherein the 0.9% isotonic solution comprises 0.025M sodium citrate.

15. The process according to claim 1, wherein
   said hypertonic treatment in step i) is performed with a solution consisting of 1.0 M NaCl and 0.05 M sodium citrate;
   said hypotonic treatment in step iii) is performed with a solution consisting of 0.05 M NaCl and 0.005 M sodium citrate.

16. The process according to claim 1 wherein,
   said hypertonic treatment in step i) is performed with a solution consisting of 1.0 M NaCl and 0.05 M sodium citrate;
   said isotonic treatment in step ii) is performed with a solution consisting of 0.9% NaCl and 0.025 M sodium citrate.

17. A *Saccharomyces*' cell wall loaded with a pharmacological substance selected from the group consisting of antibiotics, anti-inflammatories, anti-bacterials, anti-virals, anti-fungals, anti-parasitic agents and vaccines obtained according to the process of claim 4.

18. A *Saccharomyces*' cell wall loaded with oxytetracycline obtained according to the process of claim 5.

19. A *Saccharomyces*' cell wall loaded with sulphadimethoxin obtained according to the process of claim 6.

20. A *Saccharomyces*' cell wall loaded with a nutritional substance selected from the group consisting of sodium quercetin, catechin, isocatechin, aliphatic polyalcohols, polyphenols, flavans, cyanins, and resveratrol according to the process of claim 7.

21. A *Saccharomyces*' cell wall loaded with a nutritional substance selected from the group consisting of cyanocobalamin, folic acid, thiamine, α-tocopherol and ascorbic acid obtained according to the process of claim 8.

* * * * *